Figure 1:
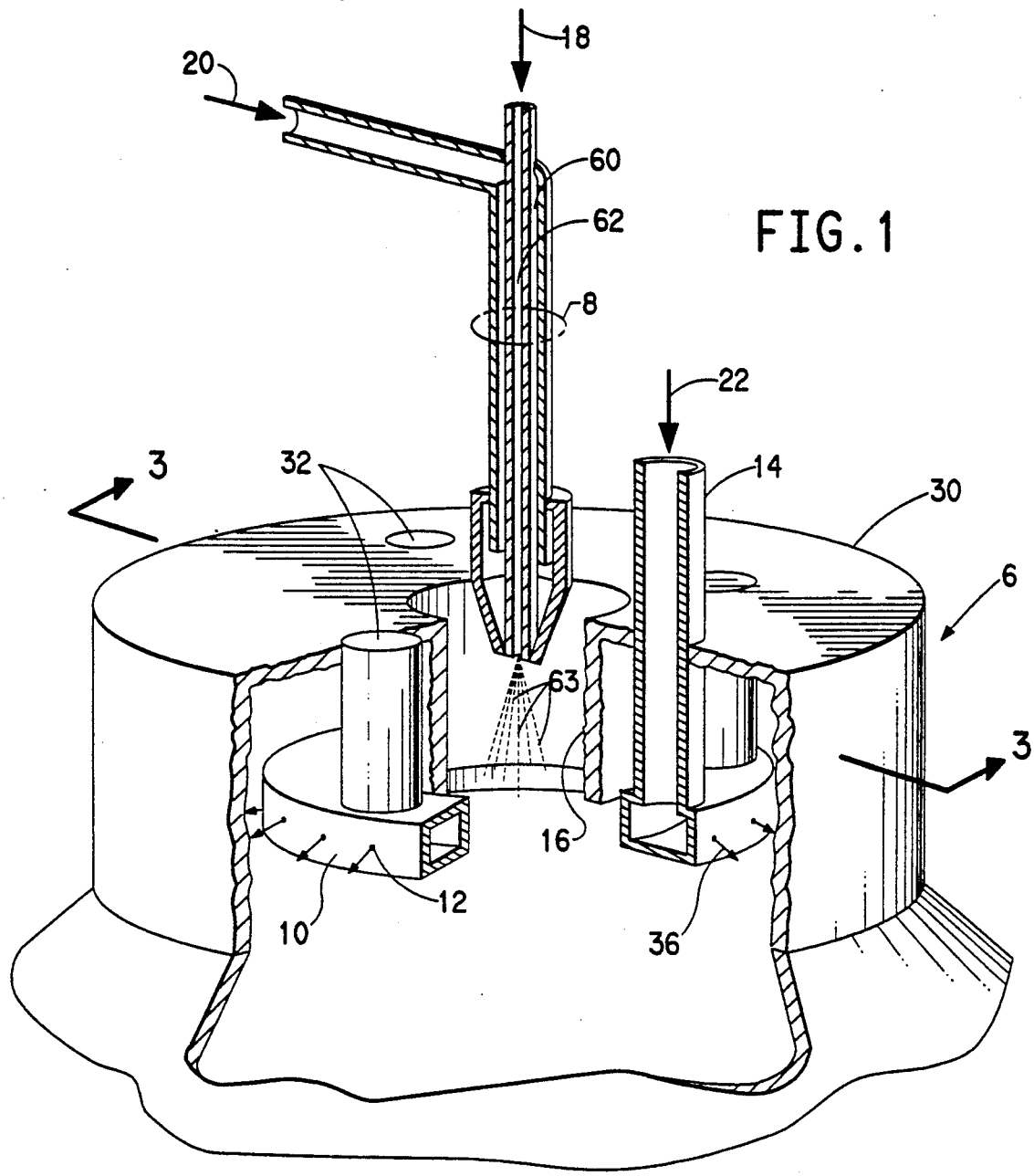

United States Patent [19]
Fawzy et al.

[11] Patent Number: 5,307,640
[45] Date of Patent: May 3, 1994

[54] APPARATUS AND METHOD FOR PRODUCING FROZEN PARTICLES OF A LIQUID

[75] Inventors: Abdel A. Fawzy, New Castle; Alferd J. Forestell, Newark, both of Del.

[73] Assignee: E. I. Du Pont de Nemours and Company, Wilmington, Del.

[21] Appl. No.: 28,380

[22] Filed: Jan. 25, 1993

[51] Int. Cl.[5] ............................................. F17C 7/04
[52] U.S. Cl. .................................... 62/52.1; 62/373; 62/534
[58] Field of Search ............... 62/57, 74, 123, 533, 62/534, 52.1, 373

[56] References Cited

U.S. PATENT DOCUMENTS

| | | | |
|---|---|---|---|
| 3,294,672 | 12/1966 | Torobin | 62/123 X |
| 3,670,520 | 6/1972 | Bonteil | 62/57 X |
| 3,928,566 | 12/1975 | Briggs et al. | 424/94 |
| 4,761,962 | 8/1988 | Andersson | 62/74 X |
| 4,838,039 | 6/1989 | Knodel | 62/534 X |
| 4,952,224 | 8/1990 | Lilakos | 62/534 |

FOREIGN PATENT DOCUMENTS

| | | |
|---|---|---|
| 0478118A1 | 7/1991 | European Pat. Off. . |
| 2256790 | 6/1974 | Fed. Rep. of Germany . |
| 1559920 | 12/1977 | Italy . |

Primary Examiner—William E. Tapoicai

[57] ABSTRACT

This invention relates to an apparatus and process for producing frozen particles of a liquid product having a liquid product nozzle for introducing liquid product droplets to be frozen and a plurality of cryogenic nozzles for introducing a cryogenic liquid directed away from the liquid product droplets.

27 Claims, 3 Drawing Sheets

APPARATUS AND METHOD FOR PRODUCING FROZEN PARTICLES OF A LIQUID

FIELD OF THE INVENTION

This invention relates to an apparatus and method for producing frozen particles of a liquid and, more particularly, to an apparatus having a liquid nozzle for introducing liquid droplets to be frozen and a plurality of cryogenic nozzles for directing cryogenic liquid away from the liquid droplets so as to freeze the liquid droplets to produce frozen particles.

BACKGROUND ART

The formation of physically uniform and chemically homogeneous spherical frozen particles from aqueous biological solutions and suspensions is essential to the manufacture of unit dose tablets for the pharmaceutical and diagnostic industries. Physically uniform particles minimize variability in bulk density and provide for tablet manufacturing processes that can produce tablets which vary in weight by no more than about one-half percent. Homogeneous chemical composition of the particles is needed to insure an accurate unit dose. From a manufacturing perspective it is desirable for frozen particles which are processed in various types of manufacturing tablet making equipment to exhibit the free flow properties characteristic of spherical particles. Furthermore, any manufacturing process for obtaining frozen particles with these desired characteristics should operate efficiently to offset the generally high cost of reagents and other raw materials.

Known techniques used in processing granular products include dry blending, direct compression, wet granulation, particle fabrication by coating product nuclei with discrete ingredients, and spray freezing of frozen particles.

Spray freezing methods generally produce highly uniform particles as a result of their characteristically rapid freezing processes. However, spray freezing is generally an expensive technique due to the high cost of refrigerants and the relatively large product losses which can occur.

Typical methods of spray freezing include striking or impinging a solution to be frozen into or against a liquid refrigerant stream(s) or spray(s), spraying a solution to be frozen onto the surface of a bath of liquid refrigerant, and spraying solution to be frozen through a freezing zone. Examples of refrigerants typically used to accomplish this freezing include liquid nitrogen, liquid carbon dioxide, and fluorocarbons.

German Patent No. 2,556,790 filed on Nov. 20, 1972 and published Jun. 6, 1974 discloses a process for deep freezing aqueous extracts with a freezing vessel having a conical lower section which provides for the impingement of a liquid product with a liquid refrigerant. Impingement occurs by one of three disclosed variations including downwardly spraying product and upwardly spraying refrigerants, upwardly spraying both product and liquid refrigerant, and both upwardly and downwardly spraying the product and upwardly spraying the liquid refrigerant. The disadvantage of this apparatus is the likelihood that frozen product will adhere to the liquid refrigerant nozzles and the funnel shaped bottom of the spray chamber, thus resulting in yield losses.

U.S. Pat. No. 4,952,224, issued Aug. 28, 1990, discloses an apparatus having a downwardly directed spray of atomized liquid fat and a radially inwardly directed plurality of individual spray jets of liquid nitrogen or carbon dioxide which surround and impinge against the downwardly directed spray of liquid fat droplets. The individual spray jets of this apparatus are likely to produce non-uniform agglomerations of the product due to the high velocity contact of the liquid refrigerant and the product. In addition, due to the limited time that the product is in contact with the liquid refrigerant, at least some product is unlikely to be frozen.

Italian Patent No. 2,659,546 issued Jul. 18, 1985, discloses an apparatus for freezing food products having an insulated freezing chamber with a conical lower section and a liquid refrigerant nozzle with a vertically downward directed spray located in the top center of the chamber. A plurality of product nozzles are distributed around and directed at the sides of the central refrigerant spray. Using this apparatus it is likely that unacceptably high particle size variations would occur during a continuous manufacturing process due to variations likely to occur in product supply and control systems, such as pressure changes in the product supply pump and pulsations within the nozzles.

U.S. Pat. No. 3,928,566 issued on Dec. 23, 1975 discloses an apparatus for freezing biological solutions in a moving stream of fluorocarbon refrigerant. The solutions are sprayed into this moving stream of fluorocarbon refrigerant from a plurality of small diameter syringe needles and the frozen particles are subsequently collected by skimming the surface of the bath with a collection device. This process has the disadvantage of forming particles of varying shape and uniformity. Further, the selection of the liquid refrigerant is critical to the use of the process because the density of it must be greater than the solution to be frozen to prevent the frozen particles from sinking below the surface of the liquid refrigerant bath. The use of fluorocarbon refrigerants, which provide for the buoyancy of the frozen particles, is nonetheless not desirable as a result of concerns relating to environmental emissions.

European Patent Application No. 0 478 118 published Apr. 1, 1992 discloses an apparatus that produces microfine particles for use in food processing, pharmaceuticals, and semiconductors having a freezing chamber with a conical lower section, a plurality of liquid refrigerant nozzles which direct the liquid refrigerant in a clockwise or counterclockwise direction within the vessel tangential to the circumference of the vessel, and a downwardly directed product nozzle. The disclosed apparatus has the disadvantage that at least some of the liquid refrigerant is likely to be in the form of relatively large droplets, and thus likely to be lost along the sides of the vessel.

There is needed an apparatus and process for producing uniformly, shaped, homogeneous frozen particles of a liquid while minimizing product yield losses.

SUMMARY OF THE INVENTION

Many of the disadvantages of the prior art are solved by the apparatus and process of the present invention.

This invention relates to an apparatus for utilizing a cryogenic liquid for producing frozen particles of a liquid product which comprises:

(a) a housing;

(b) a liquid product nozzle for introducing droplets of the liquid product into the housing; and (c) a plurality of cryogenic liquid nozzles for introducing the cryogenic liquid into the housing directing the cryogenic liquid away from the liquid product droplets, whereby the cryogenic liquid freezes the liquid product droplets to produce frozen particles.

Another aspect of the invention relates to an apparatus for producing frozen particles of a liquid product which comprises:

(a) a housing with a vertically disposed upper cylinder having an upper diameter and a vertically disposed lower cylinder having a lower diameter larger than the upper diameter, the upper and lower cylinders connected by a truncated conical section;

(b) a liquid product nozzle for introducing droplets of the liquid product into the upper cylinder of the housing in a downward direction; and (c) a plurality of cryogenic liquid nozzles disposed in the housing about the liquid nozzle for introducing a cryogenic liquid into the housing, the nozzles being positioned to direct the cryogenic liquid radially away from the liquid product droplets, the cryogenic liquid impinging on the housing, whereby the cryogenic liquid freezes the liquid product droplets to produce frozen particles.

Yet another aspect of the invention relates to a process for utilizing a cryogenic liquid for producing frozen particles of a liquid product in a housing which comprises the steps of:

(a) introducing droplets of the liquid product into the housing; and (b) introducing the cryogenic liquid into the housing and directing the cryogenic liquid away from the liquid product droplets;

whereby the cryogenic liquid freezes the liquid product droplets to produce frozen particles.

The apparatus and process of the present invention offer significant advantages over the prior art by providing highly uniform, homogeneous frozen particles with minimum process yield losses. Yield losses are minimized during operation of the apparatus of the present invention in that the configuration of the liquid product nozzle and the cryogenic liquid nozzles provide for a uniform environment of cryogenic liquid droplets and gaseous cryogen for producing the frozen particles of liquid product within the housing of the apparatus.

BRIEF DESCRIPTION OF THE FIGURES

FIG. 1 is a perspective view, partially cut away, of an upper portion of an apparatus constructed in accordance with a preferred embodiment of this invention for producing frozen particles of a liquid;

FIG. 2 is a partially schematic representation of an apparatus for producing frozen particles using the apparatus of FIG. 1;

FIG. 3 is a cross section of FIG. 1 taken along the section lines 3—3 depicting the upper portion of the apparatus for producing frozen particles;

FIG. 4 is an alternative embodiment of the invention depicting varying angles at which a cryogenic liquid nozzle can be directed for introducing a cryogenic liquid into the apparatus of FIG. 1; and FIG. 5 is another alternative embodiment of the invention depicting an ultrasonic nozzle which can be used as a liquid product nozzle in the apparatus of FIG. 1.

DESCRIPTION OF THE PREFERRED EMBODIMENT OF THE INVENTION

There may be seen in FIGS. 1 and 2, an apparatus for producing frozen particles of a liquid product which comprises a generally cylindrical housing 6, a liquid product nozzle, such as an atomization nozzle 8, for introducing droplets of the liquid to be frozen, and a plurality of cryogenic liquid nozzles 12 for introducing a cryogenic liquid into the housing 6 in a manner that directs the cryogenic liquid away from the liquid product droplets 63, whereby the cryogenic liquid freezes the liquid product droplets 63 to produce frozen particles.

FIGS. 1 and 3 depict an atomization nozzle 8 suitable for use as the liquid product nozzle of the present invention. Such atomization nozzles 8 are known in the art and are available commercially. The atomization nozzle 8 is directed downwardly into the housing 6 so as to discharge liquid product in a vertically downward direction and designed so that a gas shown as arrow 20, such as nitrogen or air, is forced under pressure through an annular channel 60, which surrounds a centrally located tube 62, through which the liquid product, shown by arrow 18, is discharged under pressure, such that the gas 20 breaks up the discharging liquid product into the liquid product droplets 63. Nitrogen is the preferred inert gas for use in the atomization nozzle 8. The end of the atomization nozzle 8 through which the liquid product is discharged is tapered inwardly providing a thin annulus through which the gas escapes at high velocity disposed about the liquid product. Such atomization nozzles 8 are generally useful for producing droplets in the size range of about 8 to about 4300 μm.

Several examples of known types of droplet forming nozzles or atomization nozzles can be used as the liquid product nozzle, including ultrasonic nozzles, hydraulic nozzles, and pneumatic nozzles. An example of a suitable ultrasonic nozzle for use in the present invention is the Model 8700 nozzle available from Sono-Tek Corp., Poughkeepsie, N.Y. and an example of a suitable hydraulic nozzle is Model QJ+QVV-SS-00015 available from Spraying Systems Co. (Wheaton, Ill.). Pneumatic nozzles are preferred.

Referring to FIGS. 1 and 2, the preferred housing 6 has a vertically disposed upper cylinder 24 having an upper diameter and a vertically disposed lower cylinder 28 having a lower diameter larger than the upper diameter, the upper and lower cylinders connected by a truncated conical section 26 having an upper conical diameter the same as the upper diameter and a lower conical diameter the same as the lower diameter.

The upper diameter of the upper cylinder 24 should be sufficiently large to allow for the presence of a plurality of cryogenic liquid nozzles 12, the liquid product nozzle, such as an atomization nozzle 8, and a baffle 16 (if used) between the plurality of cryogenic liquid nozzles 12 and the housing 6. Use of a baffle 16 is preferred. In addition, the diameter of the upper cylinder 24 should be sufficiently large to allow for the impingement of the cryogenic liquid against the housing 6.

The truncated conical section 26 should preferably be designed so that its upper conical and lower conical diameters are chosen such that the liquid product droplets 63 are introduced into the conical section of the housing 6 in a spray pattern at about the same angle with respect to the housing 6 as the angle of the truncated conical section 26 of the housing 6. This allows the frozen particles being produced to fall freely to the lower cylinder 28 of the housing 6 without touching and adhering to the sides of the truncated conical section 26.

The lower diameter of the lower cylinder 28 is defined by the lower conical diameter of the truncated conical section 26 as described above and should be of sufficient length to enclose and direct the frozen particles and the gaseous cryogen which may have evaporated from the cryogenic liquid into the lower end of the lower cylinder 28 of the housing 6.

Preferably the apparatus is provided with a collection means 34 for the frozen particles. Any collection means 34 large enough to capture and hold the frozen particles produced in the housing 6 can be used including relatively simple devices such as trays which are manually operated as well as fully automated conveyor type systems for transporting the frozen particles away from the apparatus of the invention. The collection means 34 should be kept at a temperature below the freezing point of the frozen particles to insure that the frozen particles do not melt; such a temperature can be maintained, preferably, using the cooling effect resulting from the evaporation of cryogenic liquid to gaseous cryogen.

Preferably, a baffle 16 is included between the cryogenic liquid nozzles 12 and the atomization nozzle 8. Such a baffle 16 serves to prevent cryogenic liquid from directly striking the atomization nozzle 8 and freezing liquid product in the atomization nozzle 8 or from freezing liquid product just forming droplets at the tip of the atomization nozzle 8. The baffle 16 can be supported by any means sufficient to hold it between the atomization 8 and the cryogenic liquid nozzles 12 and should extend between the atomization nozzle 8 and the liquid cryogen nozzles 12 to a depth sufficient to serve as an impingement surface for any cryogenic liquid being projected directly from the cryogenic liquid nozzles 12.

By "liquid product" is meant any liquid which is to be frozen into uniform spherical particles. The preferred liquid products are aqueous solutions useful as diagnostic reagents or pharmaceutical reagents, including but not limited to solutions containing dissolved proteins such as enzymes, antibodies, antigens, vitamins, and hormones, solutions of other biological materials such as nucleic acids, antibiotics, and various drugs. Examples of such diagnostic reagents include aqueous solutions of biologically active substances such as nicotinamide adenine dinucleotide (NAD), which can be used in toxicology testing for analytically determining lactic acid and ethyl alcohol, and NAD-reduced disodium salt trihydrate (NADH), which can be used in analytically determining alphahydroxybutyrate dehydrogenase, the amount of which in turn can be related to the amount of the isoenzymes LD1 and LD2 of lactate dehydrogenase (LDH). These biologically active substances are preferably combined with an excipient such as mannitol or trehalose, and a lubricant such as carbowax. Other examples of suitable liquid products for use as diagnostic reagents and which can be frozen in accordance with the present invention include solutions of indicator compounds such as the organic dye dichloroindophenol, useful in determining pseudocholinesterase (PCHE), and liquid suspensions such as for example, a slurry of creatine kinase MB (CKMB) monoclonal antibody-coated chromium dioxide particles suspended in water, which can be used to test for the MB isoenzymes of creatine kinase.

One of the important aspects of the present invention is that frozen particles produced using the apparatus and process of this invention retain the biological and chemical characteristics and properties of the liquid product from which they are produced. For example, liquid products containing dissolved proteins such as enzymes can be frozen using the present invention to produce particles which retain the enzymatic activity of the aqueous liquid product.

By "liquid product nozzle" is meant any nozzle which can be used to introduce droplets of liquid product to be frozen into the apparatus of the present invention. The droplets of liquid product can vary depending on the desired frozen particle size. The liquid product nozzle therefore should be chosen so as to provide for droplets of a size sufficient to provide for the desired frozen particles. The preferred particle size range for the frozen particles produced using the apparatus of the present invention is about 75 to 600 $\mu$m.

Figure 4:
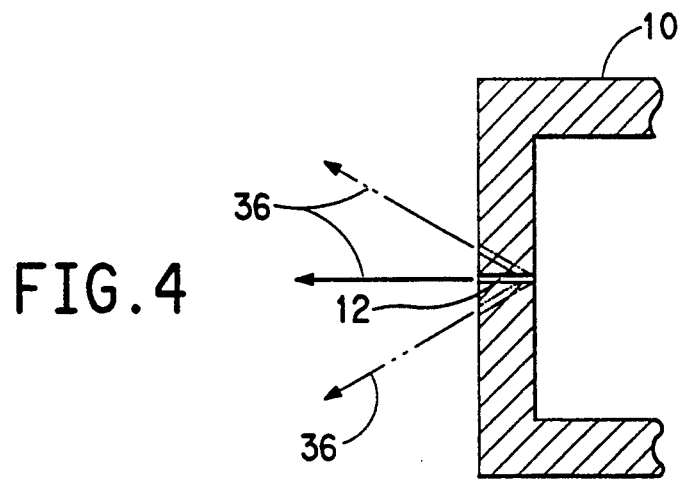
Figure 5:
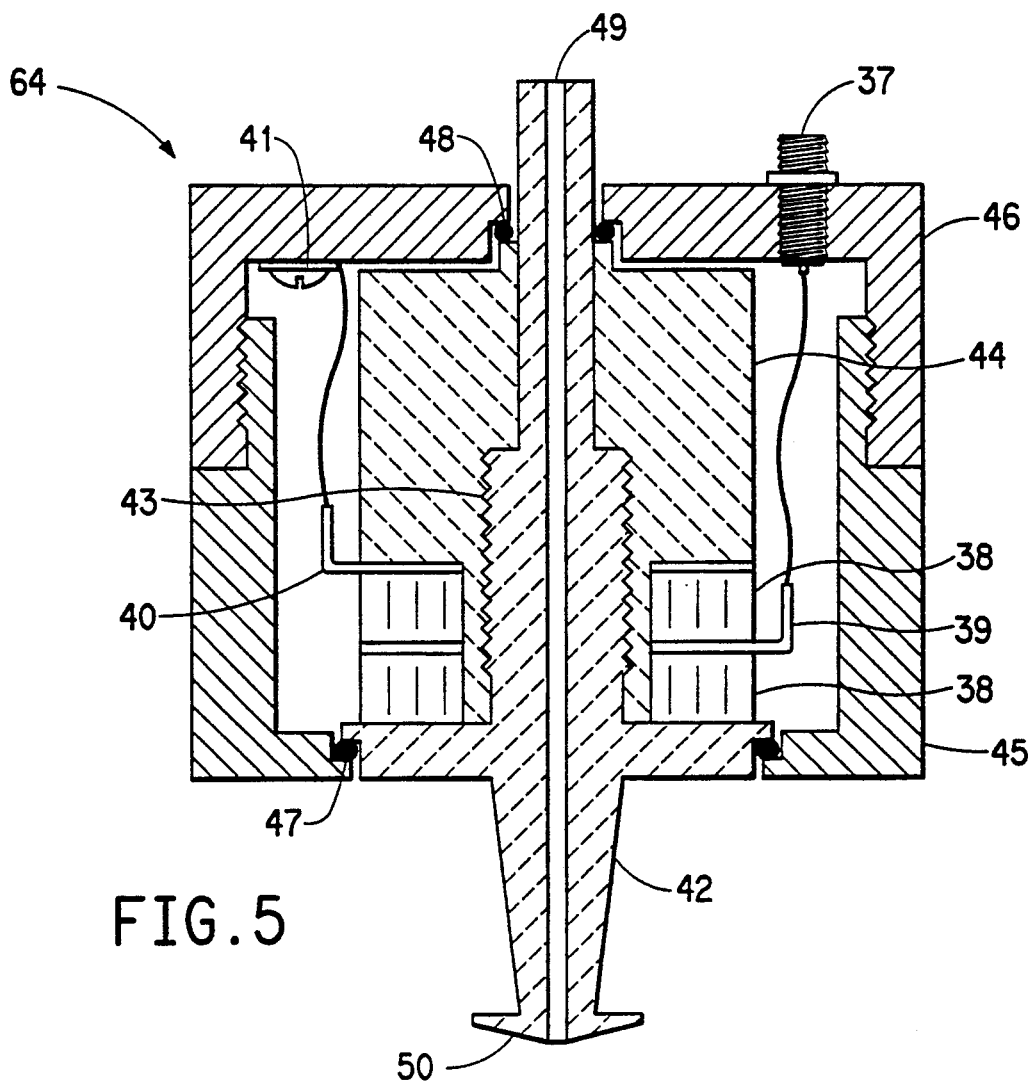

One of the important features of the present invention is that the cryogenic liquid nozzles 12 are positioned so as to introduce cryogenic liquid which is directed away from the liquid product droplets 63. The cryogenic liquid can be directed away from the liquid product droplets 63 at a transverse angle with respect to the liquid product droplets 63. Preferably the transverse angle is a 90° right angle. By directing the cryogenic liquid away from the liquid product droplets 63 the apparatus of the present invention provides for a continuous high yield manufacturing process which can produce frozen particles of a uniform spherical size and homogeneous chemical composition which do not adhere to the sides of the apparatus housing 6. FIG. 4 depicts varying angles at which a cryogenic liquid can be directed with respect to the liquid product droplets 63 discharged from a liquid product nozzle such as the atomization nozzle 8. The cryogenic liquid nozzle 12 is a hole which can be drilled at varying angles to discharge the cryogenic liquid shown by arrows 36 in various directions.

By "housing" is meant a chamber in which the liquid product droplets are frozen. The housing 6 confines any gaseous cryogen which may have evaporated from the cryogenic liquid. The housing 6 should be vented to allow for the escape of any evaporated gaseous cryogen. A suitable housing 6 for use with the present invention can have a variety of shapes including rectangular, square, and cylindrical shapes. An upper portion of the housing 6 is preferably used for the introduction of the cryogenic liquid and the liquid product droplets 63, and for the formation of the frozen particles. A lower portion of the housing 6 is preferably used for collecting the frozen particles and venting any gaseous cryogen which may have evaporated from the cryogenic liquid. The housing 6 need not be insulated; an uninsulated housing 6 is preferred.

Preferably, the housing 6 further serves as an impingement surface for the cryogenic liquid discharged from the plurality of cryogenic liquid nozzles 12. The cryogenic liquid preferably impinges or strikes the housing 6 at a 90° right angle with respect to the housing 6. A 90° right angle for the impingement of the cryogenic liquid with respect to the housing 6 is preferred because it insures the smallest cryogenic liquid droplet size.

The preferred embodiment, providing for the impingement of the cryogenic liquid against the housing 6, provides a means for the discharged cryogenic liquid to break up into relatively small droplets. This is especially useful where the cryogenic liquid is introduced into the housing 6 using a plurality of cryogenic liquid nozzles 12 which are a plurality of holes in a ring manifold 10.

The preferred cryogenic liquid nozzles 12 are a plurality of such holes in a ring manifold 10. The cryogenic liquid is introduced into the ring manifold 10, shown by 22, through a tube 14. The use of a plurality of holes drilled into a manifold for the cryogenic liquid nozzles 12 provides for the introduction of streams of cryogenic liquid shown by 36 into the housing 6, each stream corresponding to a hole in the ring manifold 10. The hole size can be varied depending upon the impingement distance from the cryogenic liquid nozzle 12 to the housing 6 (where cryogenic liquid streams are utilized they should impinge upon the housing 6 to produce droplets), and the desired droplet size. Preferably the holes should be in a size range of about 0.010 to about 0.060 inches. Such streams should be broken apart so as to form small droplets of cryogenic liquid. These droplets of cryogenic liquid should be small enough to produce the maximum amount of frozen particles for a given amount of liquid product and should be of relatively uniform and sufficiently small size to provide for a uniform environment of liquid cryogenic droplets and gaseous cryogen within the housing 6 of the apparatus in order to be useful for the continuous manufacturing of frozen particles. The cryogenic liquid droplets should be sufficiently small so that they do not run down the sides of the housing 6. The formation of cryogenic liquid droplets is important for providing for the optimal heat transfer between the cryogenic liquid and the liquid product droplets 63.

Preferably, the temperature at the lower cylinder 28 outlet is maintained at about −60° to about −70° C. This temperature range can be obtained typically by choice of cryogenic liquid and adjustment of cryogenic liquid flow rate. If this temperature range cannot be achieved, the liquid product flow rates can be adjusted so that the liquid product flow rate into the apparatus can be lowered.

Initially the liquid product flow rate can be adjusted to about 100 to about 125 milliliters per minute (ml/min) and the atomization gas pressure can be adjusted to about 0.5 pounds per square inch (psi). By adjusting liquid product flow rate and atomization pressure a desired particle size can be achieved. For example, an undesirably small particle size can be corrected by lowering the atomization pressure. Other variables which can be optimized to achieve a desired particle size include cryogenic liquid flow rate, choice of type of liquid product and cryogenic liquid nozzles 12, and choice of housing 6.

FIG. 5 depicts an ultrasonic nozzle assembly 64 suitable for use as the liquid product nozzle of the present invention. Such ultrasonic nozzle assemblies 64 are known in the art and are commercially available. Ultrasonic nozzles produce droplets of the liquid product by electrically generated vibrations of the nozzle and are typically useful for producing droplets in the size range of about 10 to about 100 μm. The ultrasonic nozzle assembly 64 has a nozzle 42 with an axially projecting threaded boss 43 and a hollow core 49. A pair of piezoelectric crystals 38, each having an associated electrode 39,40 are received on the boss 43. The crystals 38 are held in place by threading the back piece 44 onto the boss 43. The nozzle 42, crystals 38, electrodes 39,40 and back piece assembly 44 is elastically supported in the threadably engaging front housing 45 and rear housing 46 by the front and rear O-rings, 47 and 48 respectively. An ultra high frequency electrical signal is supplied to the piezoelectric crystal discs 38,39 through the connector 37 to the input electrode 39, with a ground being provided through electrode 40 to the ground lug 41. The electrical signal causes the crystals 38,39 to expand and contract at the electrical excitation frequency, thus causing the nozzle 42 and back piece 44 to vibrate by virtue of their elastic mounting on 0-rings 47 and 48. Liquid product that is introduced into the hollow core 49 absorbs some of the vibrational energy. The vibrational energy sets up wave motions in the liquid whose peaks become unstable and break away from the liquid mass beneath, causing a fine mist at the tip of the nozzle 50.

By "cryogenic liquid" is meant any liquid capable of freezing the liquid spray of reagent into particles under atmospheric conditions. Various cryogenic liquids which can be used in the present invention include nitrogen, carbon dioxide, argon and various fluorocarbons. Preferably the cryogenic liquid used is nitrogen.

By "cryogenic liquid nozzle" is meant any nozzle for introducing a cryogenic liquid into the apparatus of the present invention. By a "plurality" of cryogenic liquid nozzles is meant more than one cryogenic liquid nozzle. Preferably, four (4) or more cryogenic liquid nozzles are utilized.

Several types of nozzles are suitable for use as the cryogenic liquid nozzles of the present invention, including those useful in producing droplets such as pneumatic nozzles, ultrasonic nozzles, and hydraulic nozzles as well as simpler nozzles such as small holes in a manifold for introducing streams of liquid cryogen. The use of holes in a manifold is preferred. The following Examples serves to illustrate the invention.

EXAMPLE 1

Construction of an Apparatus for Producing Frozen Particles of a Liquid Product An example of an apparatus designed and built for producing frozen particles of a liquid product in accordance with the present invention consisted of three circular sections and a top plate 30 of FIG. 1 welded to each other.

The lower section was a 14 inch (″) diameter, 13″ high open-ended vertically disposed lower cylinder FIG. 2 (28). The truncated conical middle section, FIG. 2 (26), had a lower diameter of 14″, an upper diameter of 8″, and a height of 7″. The top section was an 8″ diameter, 4″ high open-ended vertically disposed upper cylinder, FIG. 2 (24). The top plate, FIG. 1 (30), consisted of an 8″ diameter disk with a 3″ diameter hole in its center and a 1.5″ baffle, FIGS. 1 and 3 (16), extending downward.

All of the sections including the top plate 30 of the vessel were constructed using 0.05″ thick, 304 grade stainless steel and the entire vessel was mounted vertically in a laboratory hood.

The cryogenic liquid nozzles, FIG. 1, (12), were holes drilled in a hollow ring manifold, FIG. 1 (10), with an inside diameter of 4″, an outside diameter of 5.5″, and a 1″ by ¾″ rectangular shaped cross section using 0.060″ thick 304 stainless steel. The cryogenic liquid nozzles 12 were thirty-six (36), 0.036 diameter, equally spaced holes, FIG. 1, (12), centered around the outside of a ring manifold, FIG. 1 (10), the nozzles 12 were disposed about the atomization nozzle 8, and the cryogenic liquid nozzles 12 were drilled at a 90° right angle radially outward with respect to the ring manifold 10.

The cryogenic liquid was introduced into the housing 6 of the apparatus by forcing it through the hollow interior of the ring manifold 10 and out of the nozzle holes FIG. 1 (36).

Three equally spaced 1 inch long, ¾ inch diameter vertical posts, FIG. 1 (32), were attached to the top of the ring manifold 10 to support it within the housing 6. The bottom portion of the posts were welded to the ring. The top portion of the posts were drilled and tapped for ¼-20×¾ inch screws which provided a means for centrally mounting the ring manifold 10 to the top plate 30 of the vessel. A conventional bulk head fitting (not shown) was also attached to the top of the ring manifold 10 which allowed a one-half inch diameter cryogenic liquid feed line, FIGS. 1 and 3 (14), to be attached to and supply cryogenic liquid, FIGS. 1, 2, and 3 (22), to the hollow interior of the ring manifold 10.

The liquid product nozzle was a pneumatic atomization nozzle FIG. 1 (8), with a 1.1 millimeter (mm) opening, (Glatt Air Techniques, Ramsey, N.J.). The atomization nozzle 8 was centrally mounted using a ring stand in the central hole of the top plate 30 such that the tip of the atomization nozzle 8 was one inch below the top of the top plate 30. A positive displacement pump, Drive Model Number 7617-60, Pump Head Model Number 1840-00, (Cole-Parmer Instrument Company, Chicago, Ill.) was used to feed the liquid product to the atomization nozzle 8 in order to minimize pressure pulsations at the atomization nozzle 8.

EXAMPLE 2

Producing Frozen Particles of a Trehalose Solution

Liquid nitrogen from a 200 pound (lb.) tank was fed through a one-half inch diameter flexible steel tube at an initial flow rate of 1 kilograms per minute (Kg/min) through a conventional metering valve (Keen Gas Corporation, Wilmington. Del.) to the ring manifold 10 having the cryogenic liquid nozzles 12 drilled into it. Liquid nitrogen was thereby forced out of the cryogenic liquid nozzles FIG. 1 (12). The metering valve was adjusted until the steady state temperature measured centrally at the extreme bottom of the housing 6 was in the range of −60 to −70 degrees C. (°C.). An 18 inch square 2.0 inch deep collection tray (FIG. 2 (34) was pre-chilled to −350° C. and placed about 3" to 4" below the opening of the vessel.

Figure 2:
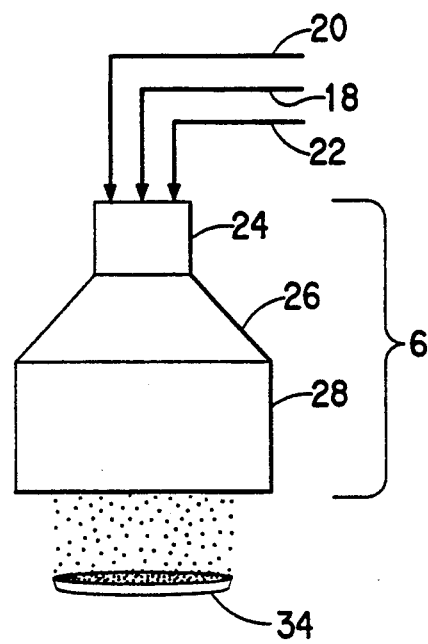
Figure 3:
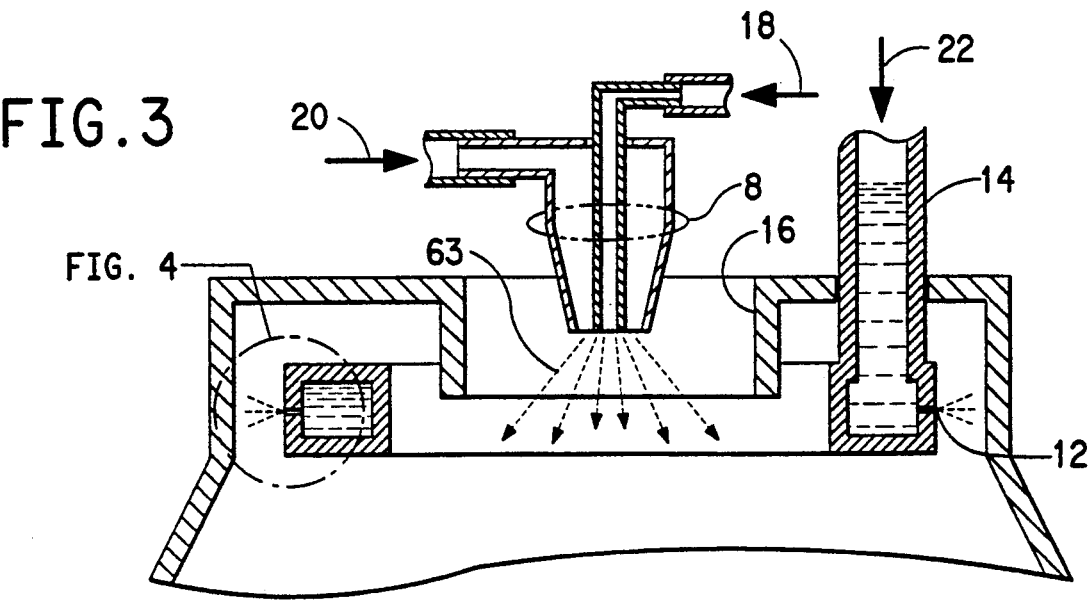

Nitrogen gas at a pressure of 0.8 pounds per square inch (psi), FIGS. 1,2, and 3 (20), and an aqueous solution of 27.5% trehalose (Segma AF Corporation, St. Louis, Mo.) and Carbowax (Union Carbide Corporation, Houston, Tex.) at a flow rate of 125 milliliters per minute (ml/min), FIGS. 1,2, and 3 (18), was fed to the atomization nozzle 8.

The frozen particles were collected in the collection tray 34 and manually distributed in the tray 34 to form a uniformly thick layer of frozen liquid product particles about 1 and ½" deep. The liquid product and nitrogen gas flows to the atomization nozzle 8 were stopped and the production run of frozen particles was completed.

The above described process using the apparatus of FIGS. 1, 2, and 3 provided spherical frozen particles with an average size of about 400 microns, with a size range of about 75 to 590 microns (μm), and a surface area of 17 square meters/gram. To produce particles of this size range for salt or protein containing solutions, a lower liquid product flow rate should be used as these solutions can take longer to freeze, and a lower flow rate allows the liquid product droplets to remain within the apparatus, and therefore in the presence of the cryogenic liquid for a longer period of time.

EXAMPLE 3

Producing Frozen Particles of A CKMB Diagnostic Reagent Useful in a Creatine Kinase-MB (CKMB) Immunoassay Into a 15 liter (L) stainless steel pot was added 3850 milliliters (ml) of deionized water. The following components were added, mixed, and allowed to dissolve in order: 838 g trehalose (Segma AF, St. Louis, Mo.), 220 g polyethylene glycol (PEG 8000) (Segma AF, St. Louis, Mo.), 500 g bovine albumin (Miles Inc., Kankakee Ill.), 585 g sodium chloride (VWR Scientific, Bridgeport N.J.), 4.1 g magnesium chloride (VWR) Scientific, Bridgeport N.J.), 590 g disodium PIPES buffer, (Research Organics Inc., Cleveland Ohio), 90 g PIPES (Research Organics Inc., Cleveland Ohio), 360 ml of a CKMB conjugate solution consisting of 1:1 ratio of F(ab')$_2$ anti-CKMB antibody fragments and $\beta$-galactosidase (prepared as described below), and 2.5 g mouse IgG antibody (Scantibodies Laboratory, Santtee, Calif.) to eliminate non specific binding.

The cell lines producing the monoclonal antibodies employed were obtained using the procedure described in U.S. Pat. No. 4,912,033 and in Vaidya et al., Clin. Chem. 32(4): 657–663 (1986),the disclosures of which are hereby incorporated by reference.

The anti-CKMB monoclonal antibodies so obtained were purified and isolated using affinity chromatography on Protein A Sepharose (Pharmacia Fine Chemicals, Uppsala, Sweden). Protein A is a polypeptide (MW 42,000) isolated from Staphylococcus aureus which binds immunoglobulin without interacting with the antigen binding site.

While the above described method is preferred, monoclonal antibodies can be purified using any number of standard techniques such as ammonium sulfate precipitation dialysis, affinity chromatography, ion exchange chromatography, etc. These and other methods for the isolation and purification of monoclonal antibodies are described in general by Goding, Monoclonal Antibodies: Principles and Practice, Academic press, London and New York, 1983 and in U.S. Pat. No. 4,533,496 the disclosures of which are hereby incorporated by reference.

The anti-CKMB monoclonal antibody used to produce the immunoreactive fragment described below was obtained as described above. The clone number was 2580 CC 4.2, and the monoclonal antibody was an IgG2b subclass.

The purified anti-CKMB monoclonal antibody was dialyzed overnight at 4 degrees C. (°C.) against an acetate buffer containing 100 millimolar (mM) sodium acetate and 150 mM sodium chloride, pH 3.5. The dialyzed antibody solution was diluted to a concentration of 5 milligrams per milliliter (mg/ml) using the acetate buffer. The antibody solution was placed in a water bath at 37° C. for about 5 to 10 minutes.

A 10 mg/ml solution of pepsin (Sigma Chemical Co., St. Louis, Mo.) was prepared in the acetate buffer. The amount of pepsin required to give a weight ratio of antibody to pepsin of 50:1 was determined and the determined amount of pepsin solution was added to the antibody solution as the antibody solution was stirred. The mixture was incubated for about 10-15 minutes. The reaction was then stopped by slowly adding 3.5 molar (M) Tris base drop wise until the pH of the solution was in the range of 7.0 to 8.0. The resulting F(ab')$_2$ preparation was then passed through 15-20 ml of Sepharose having Protein A bound to it in a 2.2×25 centimeter (cm) column at a flow rate of about 4-4.5 ml per hour. The protein peak was monitored by recording the absorbance of the fractions at 280 nm. The protein peak was collected and concentrated to about 30 mg/ml using an Amicon stirred cell fitted with a 62 mm PM 30 membrane filter (both purchased from the Amicon Corp.). The sterilized F(ab')$_2$ concentrate was filtered and stored at $-20°$ C.

The sterilized F(ab')$_2$ concentrate was coupled to $\beta$-galactosidase to produce a F(ab')$_2$ $\beta$-galactosidase conjugate using the procedure substantially as described by Kitagawa et al., Enzyme labeling with N-hydroxysuccinimidyl ester of maleimide in "Enzyme Immunoassays," Ishikawa et al., Eds., pp 81-90 (1981), the disclosure of which is hereby incorporated by reference. Anti-CKMB monoclonal antibody F(ab')$_2$ fragment was dialyzed against an antibody dialysis buffer containing 20 mM phosphate buffer, 300 mM NaCl, pH 7.0). One mole of F(ab')$_2$ was mixed with 30 moles of N-succinimidyl,4(N-maleimido methyl) cyclohexane-1-carboxylate (SMCC) and incubated at room temperature for 35 min. with constant stirring. The mixture was loaded on a Sephadex G-25 column (2.2×13 cm) equipped with the UV detector (absorbance 280 nm). The activated F(ab')$_2$ fragment was eluted using the antibody dialysis buffer. The protein peak was collected, its volume recorded and the protein concentration estimated. One mole of E. coli $\beta$-galactosidase (Boehringer Mannheim) equivalent to 1 mole of SMCC activated F(ab')$_2$ was dissolved in the antibody dialysis buffer. Activated F(ab')$_2$ was mixed with $\beta$-galactosidase and incubated for at least 25 minutes at 25° C. with constant stirring. Synthesis of the conjugate was monitored using an HPLC (LKB) equipped with a 100 $\mu$l loop GF 450 analytical column. The reaction was quenched when the leading peak extended beyond the second peak on the chromatogram by adding 10 $\mu$l of 0.1M N-ethylmaleimide solution for every ml of conjugate reaction mixture. The mixture was concentrated to 4.0 ml using an Amicon stir cell and YM 100 filter (both purchased from the Amicon Corp.). Conjugate concentrate was filtered through 0.2 $\mu$ syringe filter and purified using LKB HPLC equipped with 1 ml loop GF 450 column, UV monitor, fraction collector and chart recorder. Appropriate fractions were collected and pooled and absorbance was measured at a wavelength of 280 nm to estimate the protein concentration. The resulting concentrate was filtered, sterilized and stored at 4° C. Conjugate concentrate was diluted as needed in a $\beta$-galactosidase conjugate dilution buffer (33.5 g PIPES (piperazine-N,N'-bis(2-ethanesulfonic acid)) 0.2 g MgCl$_2$, 29.2 g NaCl, 100 g bovine serum albumin, and 0.167 g mouse IgG per liter of deionized water, pH 7.0) for the CKMB assay.

The solution was adjusted to a final volume of 11L with deionized water and filtered through a 5 $\mu$m filter (Gelman Sciences, Annarbor Mich. (product No. T 505141).

The apparatus and its operation was the same as that of Examples 1 and 2 with the exception that 0.5 pounds per square inch (psi) was used for the atomization gas pressure.

The average particle size was determined to be 315 microns by filtering the particles through a series of known size sieves, with the size distribution shown in Table 1.

TABLE 1

| Size (microns) | % of total particles |
|---|---|
| >590 | 9.4 |
| 505-590 | 19.2 |
| 335-504 | 27.8 |
| 215-334 | 16.4 |
| 165-215 | 10.2 |
| 110-164 | 12.2 |
| 75-109 | 4.8 |

$\beta$-galactosidase activity of the above liquid product was measured both before and after spray freezing using the aca ® discrete clinical analyzer (E.I. duPont de Nemours and Company, Wilmington, Del. 19898). The pre spray freezing sample was obtained by diluting 1 mL of the liquid product with 20 mL of water. A post freezing sample was obtained by dissolving 1 gm of the frozen liquid product in 4 mL of water and diluting this solution with 80 mL of water. The prepared samples were placed in standard aca sample cups. The sample cups along with 3 aca MCKMB packs (standard aca ® discrete clinical analyzer packs available from E.I. Du Pont de Nemours and Company, Wilmington, Del.) were loaded on the aca. The aca dispensed 100 $\mu$l of sample, 2 mL of phosphate buffer, pH 7.8, and 2.9 mL of water into each MCKMB pack. Breaker mixer 1, a component of the aca ® discrete clinical analyzer which breaks tablet reagents in the pack and facilitates the mixing of the reagents, was utilized to dissolve and mix the pack reagents with the sample. Bound enzyme reacted with chlorophenol red galactoside(CPRG) contained in the pack reagents at 37° C. to form chlorophenol red(CPR). After 4.2 minutes the absorbance of the contents of the pack was measured at 577 and 600 nm wavelengths. 577 was the primary wavelength at which the CPR has maximum absorbance, and 600 nm was the blanking wavelength. The 600 nm reading was subtracted from the 577 reading to eliminate interference due to suspended particles and the resulting average absorbance number was multiplied by 20 due to the 1 to 20 dilution of the sample. The results, shown in Table 2 indicate minimal loss of enzymatic activity due to spray freezing. Thus the usefulness of the present invention in producing frozen particles of diagnostic reagents which retain their biological activity upon freezing has been demonstrated.

TABLE 2

| Conjugate | mA | mA | mA | mean | mean X dilution facter ... | % loss |
|---|---|---|---|---|---|---|
| liquid | 281.6 | 278.1 | 273.4 | 277.7 | 5554.0 | 0 |
| frozen particles | 270.9 | 275.0 | 277.5 | 274.47 | 5489.3 | 1.16 |

What is claimed is:

1. An apparatus for utilizing a cryogenic liquid for producing frozen particles of a liquid product which comprises:
   (a) a housing;

(b) a liquid product nozzle for introducing droplets of the liquid product into the housing; and (c) a plurality of cryogenic liquid nozzles for introducing the cryogenic liquid into the housing, said cryogenic nozzles directing the cryogenic liquid away from the liquid product droplets, whereby the cryogenic liquid introduced into the housing forms cryogenic liquid droplets and gaseous cryogen thereby freezing the liquid product droplets to produce frozen particles.

2. The apparatus of claim 1 wherein the liquid product droplets are downwardly directed.

3. The apparatus of claim 1 wherein the liquid product nozzle directs the droplets in a first direction and the cryogenic liquid nozzle directs the cryogenic liquid at a transverse angle with respect to the liquid product droplets.

4. The apparatus of claim 3 wherein the transverse angle is a right angle.

5. The apparatus of claim 1 wherein the cryogenic liquid impinges upon the housing at a fixed angle.

6. The apparatus of claim 5 wherein the fixed angle is a right angle.

7. The apparatus of claim 1 wherein the housing has a baffle located between the liquid product nozzle and the plurality of cryogenic liquid nozzles to prevent freezing of the liquid product in the liquid nozzle.

8. The apparatus of claim 1 wherein the cryogenic nozzles are disposed about the liquid product droplets.

9. The apparatus of claim 1 wherein the liquid product nozzle is an atomization nozzle.

10. The apparatus of claim 1 wherein the liquid product nozzle is an ultrasonic nozzle.

11. The apparatus of claim 1 wherein the plurality of cryogenic liquid nozzles is a plurality of holes in a ring manifold.

12. The apparatus of claim 1 wherein the housing has a vertically disposed upper cylinder having an upper diameter, and a vertically disposed lower cylinder having a lower diameter larger than the upper diameter, the upper and lower cylinders connected by a truncated conical section.

13. The apparatus of claim 1 wherein the apparatus has a collection means for the frozen particles.

14. An apparatus for producing frozen particles of a liquid product which comprises:

(a) a housing with a vertically disposed upper cylinder having an upper diameter and a vertically disposed lower cylinder having a lower diameter larger than the upper diameter, the upper and lower cylinders connected by a truncated conical section;

(b) a liquid product nozzle for introducing droplets of the liquid product into the housing in a downward direction; and (c) a plurality of cryogenic liquid nozzles disposed in the housing about the liquid nozzle for introducing a cryogenic liquid into the housing, the nozzles being positioned to direct the cryogenic liquid radially away from the liquid product droplets, the cryogenic liquid impinging on the housing, whereby the cryogenic liquid introduced into the housing forms cryogenic liquid droplets and gaseous cryogen thereby freezing the liquid product droplets to produce frozen particles.

15. The apparatus of claim 14 wherein the cryogenic liquid is directed away from the liquid product droplets at a right angle with respect to the liquid product droplets.

16. The apparatus of claim 14 wherein the cryogenic liquid impinges upon the housing at a right angle with respect to the housing.

17. The apparatus of claim 14 wherein the housing has a baffle disposed circumferentially about the liquid product nozzle and parallel with the vertically disposed upper cylinder located between the liquid product nozzle and the plurality of cryogenic nozzles to prevent freezing of the liquid in the liquid product nozzle.

18. The apparatus of claim 14 wherein the plurality of cryogenic nozzles is disposed circumferentially about the liquid product droplets.

19. The apparatus of claim 14 wherein the liquid product nozzle is an atomization nozzle.

20. The apparatus of claim 14 wherein the plurality of cryogenic liquid nozzles is a plurality of holes in a ring manifold.

21. A process for utilizing a cryogenic liquid for producing frozen particles of a liquid product in a housing which comprises the steps of:

(a) introducing droplets of the liquid product into the housing; and (b) introducing the cryogenic liquid into the housing and directing the cryogenic liquid away from the liquid product droplets;

whereby the cryogenic liquid introduced into the housing forms cryogenic liquid droplets and gaseous cryogen thereby freezing the liquid product droplets to produce frozen particles.

22. The process of claim 21 wherein the liquid product is an aqueous solution.

23. The process of claim 22 wherein the aqueous solution contains proteins.

24. The process of claim 21 wherein the liquid product particles have a diameter of about 75 to 590 microns.

25. The process of claim 21 wherein the liquid product particles are spherical.

26. The process of claim 21 wherein the cryogenic liquid is directed away from the liquid product droplets at a right angle with respect to the liquid product droplets.

27. The process of claim 21 wherein the cryogenic liquid is disposed circumferentially about the liquid product droplets.

* * * * *